United States Patent [19]

Kopans

[11] Patent Number: 4,962,515
[45] Date of Patent: Oct. 9, 1990

[54] RIDGED COMPRESSION ASSEMBLY FOR MAMMOGRAPHY APPARATUS

[75] Inventor: Daniel B. Kopans, Waban, Mass.

[73] Assignee: The General Hospital Corporation, Boston, Mass.

[21] Appl. No.: 435,613

[22] Filed: Nov. 13, 1989

[51] Int. Cl.⁵ .............................................. A61B 6/04
[52] U.S. Cl. ....................................... 378/37; 378/208
[58] Field of Search ................................. 378/208, 37

[56] References Cited

U.S. PATENT DOCUMENTS

| | | | |
|---|---|---|---|
| 3,824,397 | 7/1974 | Bauer et al. | 250/320 |
| 3,971,950 | 7/1976 | Evans et al. | 250/451 |
| 3,991,316 | 11/1976 | Schmidt et al. | 250/439 |
| 4,090,084 | 5/1978 | Epstein et al. | 250/439 |
| 4,259,585 | 3/1981 | Novak et al. | 250/456 |
| 4,563,768 | 1/1986 | Read et al. | 378/37 |
| 4,599,738 | 7/1986 | Panetta et al. | 378/37 |
| 4,618,973 | 10/1986 | Lasky | 378/37 |
| 4,691,333 | 9/1987 | Gabriele et al. | 378/37 |
| 4,821,727 | 4/1989 | Levene et al. | 128/653 |

FOREIGN PATENT DOCUMENTS 0146511 6/1985 European Pat. Off. .
0288187 10/1988 European Pat. Off. .

*Primary Examiner*—Craig E. Church
*Attorney, Agent, or Firm*—Lahive & Cockfield

[57] ABSTRACT

Disclosed is a breast compression assembly for an mammography apparatus and a breast compression plate for use in such apparatus. The assembly includes a first compression plate having a first compression surface extending from an input edge thereof and a second compression plate having a second compression surface extending from an input edge thereof. At least one of the compression plates includes an associated ridge member affixed to its input edge. The ridge member extends beyond the surface of the associated compression plate in the direction substantially perpendicular to the compression surface of the plate. The device further includes means for positioning the first and second compression plates, and means for selectively controlling the separation between the compression surfaces of the plates along a reference axis substantially perpendicular to the compression surfaces of the plates.

18 Claims, 3 Drawing Sheets

RIDGED COMPRESSION ASSEMBLY FOR MAMMOGRAPHY APPARATUS

BACKGROUND OF THE INVENTION

The present invention relates to mammography, and more particularly, to means for compressing and retaining breast tissue in preparation for imaging analysis.

Early detection of breast cancer relies on high quality mammography. In order to achieve this in the prior art, the breast is compressed between an x-ray detector or imager and a rigid compression plate. Compression of the breast tissue is necessary to retain the tissue and to spread the internal structures of the breast, to reduce motion of the breast, to reduce x-ray dose required of thicker tissue, and to position the breast correctly over the detector so that as much tissue as possible can be imaged at one time. In addition, forcing the breast tissues closer to the detector improves the geometric sharpness of the image obtained and evens out the exposure.

Prior mammography systems have generally included compression devices. For example, in U.S. Pat. No. 3,824,397, a plastic sheet has been used to applied pressure to breast tissue. However, uniform pressure over the entire breast cannot be obtained with this device. U.S. Pat. No. 4,090,084 provides a mounted pressure plate for the application of uniform pressure. However, compression with a flat plate can result in the breast tissue being squeezed out of the x-ray field back towards the chest wall. The result is that tissue which may contain a tumor is not imaged. Another device is described in U.S. Pat. No. 3,971,950 wherein a compression paddle with a curved surface is used to exert a variable force and is adjustable in a plurality of directions so an image of a selective view may be obtained. However, this device does not provide for the imaging of tissue pushed out of the scope of the detection device at the chest wall.

Accordingly, the object of the present invention is to provide a support/compression device for mammography which prevents the slippage of breast tissue from the field of view of the x-ray detector or imager.

Another object of the invention is to provide a compression device which enables the application of uniform pressure to the entire breast without allowing the escape of breast tissue outside of the pressure field.

Yet another object is to enlarge the field of view of an x-ray detector to cover as much of an entire breast as possible.

These and other objects of the invention will be apparent from the description, drawing, and claims that follow.

SUMMARY OF THE INVENTION

Briefly, the invention is directed to a breast compression assembly for a mammography apparatus and to a breast compression plate for use therein. It has been determined that with the use of the invention, breast tissue can be spread and held firmly and securely in place over an x-ray detector or imaging device such that none of the breast tissue escapes examination by irradiation.

The support assembly includes a first compression plate having a first compression surface extending from an input edge thereof, and a second compression plate having a second compression surface extending from an input edge thereof. At least one, and preferably both of the compression plates includes an associated ridge member extending from or affixed to its input edge. The ridge member extends beyond the surface of the associated plate in the direction substantially perpendicular to the surface of the plate at its input edge.

In one embodiment of the invention, the first compression plate further includes an integral x-ray detector.

The assembly also includes a mechanical assembly for positioning the first and second compression plates whereby the compression surface of the first compression plate is opposite to the compression surface of the second compression plate, and whereby the input edges of the first compression plate and the second compression plate are substantially opposite each other.

Also provided is a means for selectively controlling the separation between the surfaces of the plates along a reference axis substantially perpendicular to the compression surfaces. A breast inserted between the input edges of the compression plates may be captively held and compressed between the opposing compression surfaces by biasing the first and second compression plates towards each other and against the inserted breast.

BRIEF DESCRIPTION OF THE DRAWING

The foregoing and other objects of the present invention, the various features thereof, as well as the inventions thereof may be more fully understood from the following description when read together with the accompanying drawings in which.

DESCRIPTION OF THE INVENTION

Figure 1:
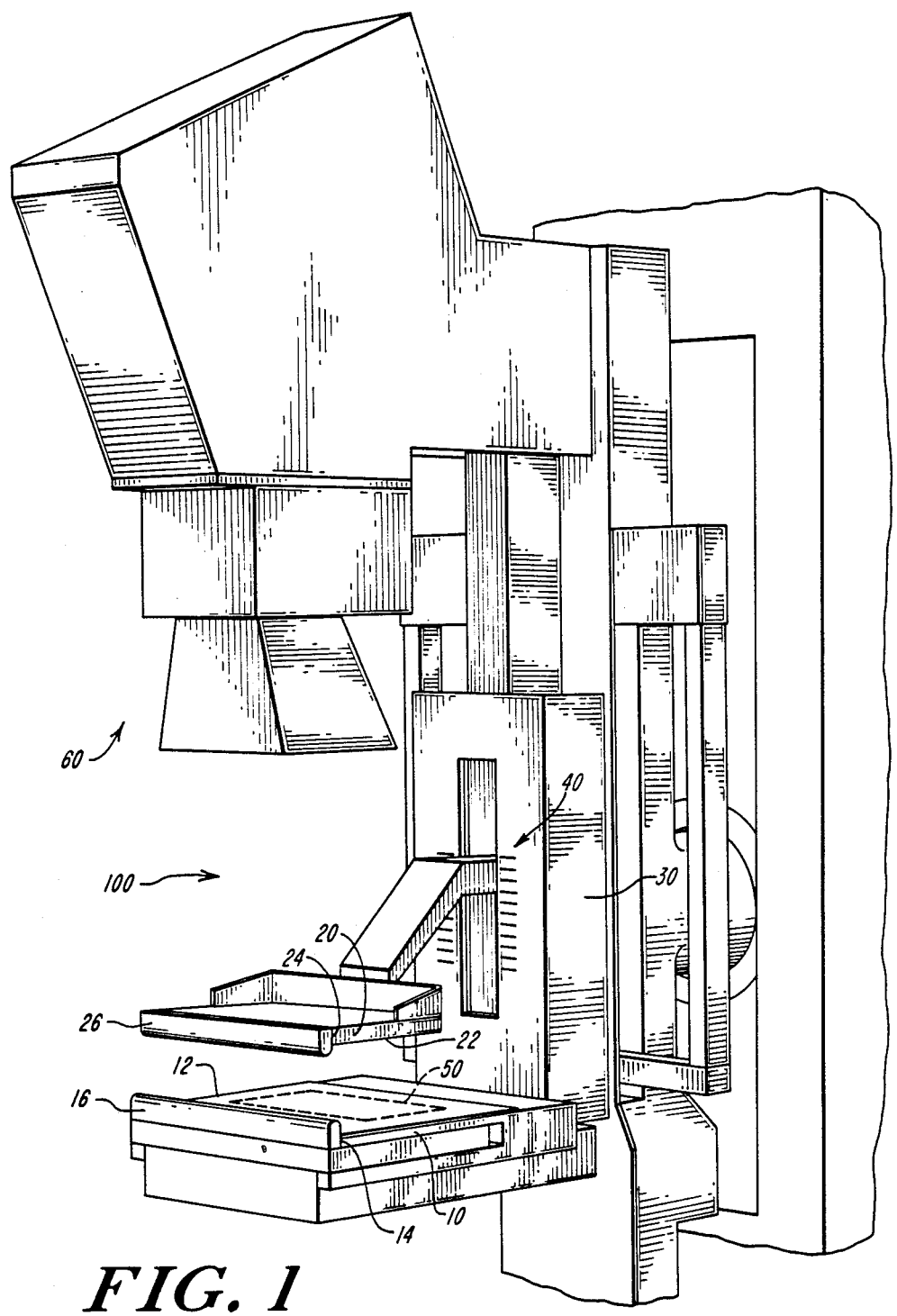
FIG. 1 shows a perspective view of an exemplary mammography apparatus including an embodiment of the breast compression assembly of the present invention.

FIG. 1 shows a perspective view of an exemplary mammography apparatus including an embodiment of the breast compression assembly 100 of the present invention. The breast compression assembly 100 includes an adjustable height first compression plate 10 and adjustable height second compression plate 20. Preferably, one or both of the plates 10 and 20 are substantially optically transparent to permit visual monitoring of a breast positioned between those plates.

First compression plate 10 has a first compression surface 12 extending from input edge 14. Rounded ridge member 16 is affixed to input edge 14 and extends beyond first surface 12 in a direction substantially perpendicular to first surface 12 at its input edge. Second compression plate 20 has a second compression surface 22 extending from input edge 24. Rounded ridge member 26 is affixed to input edge 24 and extends beyond second surface 22 at least partially in a direction substantially perpendicular to second surface 22 at its input edge. In the illustrated embodiment, compression surfaces 12 and 22 are substantially planar, although in other embodiments, curved surfaces may be used.

First compression plate 10 and second compression plate 20 are positioned such that first surface 12 of first compression plate 10 is opposite and substantially parallel to second surface 22 of second compression plate 20, and input edges 14 and 24 are substantially opposite each other. In the illustrated embodiment, plates 10 and 20 are captively held for motion along vertical tracks in a support element 30. The separation between first surface 12 and second surface 22 along a reference axis substantially perpendicular to surfaces 12 and 22 is Controlled by a control assembly in a conventional manner.

An x-ray generating device 60 is positioned above second compression plate 20. Detector means 50 such as a cassette of x-ray film is indicated by the dotted line in first compression plate 10. An imaging device other than an x-ray generator such as an NMR device may be similarly employed.

In use, the position of first compression plate 10 is initially adjusted to match the position of the underside of the breast of the patient being examined. The breast is inserted into the region between compression plates 10 and 20. Second compression plate 20 is then moved to capture and compress the inserted breast tissue while pulling the breast away from the patient's chest wall.

Figure 2A:
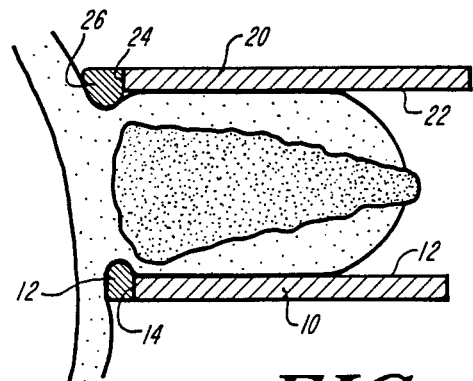
FIG. 2A shows a cross-sectional view of the first and second compression plates of the breast compression assembly of FIG. 1 in use.
Figure 2B:
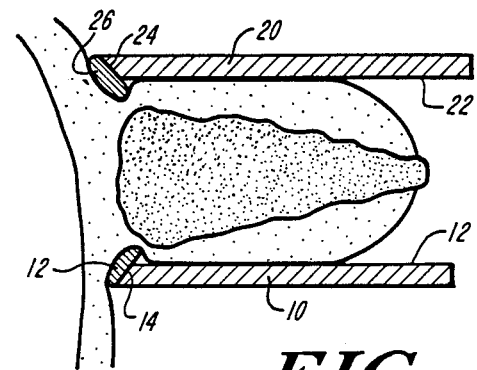
FIG. 2B shows a cross-sectional view of another embodiment of the invention wherein the ridge members are angled.
Figure 3:
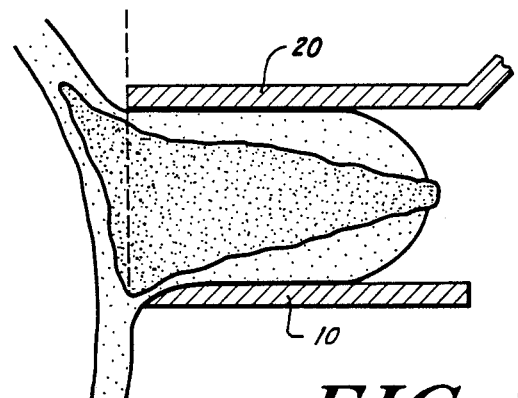
FIG. 3 shows a cross-sectional view of the first and second compression plates of a prior art breast compression assembly in use.

Because of the conical shape of the breast it is desirable to initially compress the back of the breast at the chest wall side, thereby blocking escape of tissue from the field of view. As shown in FIGS. 2A and 2B, the device of the present invention accomplishes this blockage with the use of second compression plate 20 having a rounded ridge 16 along the chest wall that protrudes towards the breast. A similar ridge 26 on first compression plate 10 improves the barrier. As compression is applied, ridge member 16 contacts the back of the breast first, and the pressure between ridge 26 and second compression plate 20 on the other side of the breast prevents the breast tissue from being squeezed out of the compression assembly. In FIG. 2B the ridge members 12 and 26 are angled inward towards the breast. For comparison purposes, FIG. 3 shows a prior art configuration (i.e., without the ridge members) wherein a breast is incompletely held in position between a support plate and a second compression plate.

Figure 4:
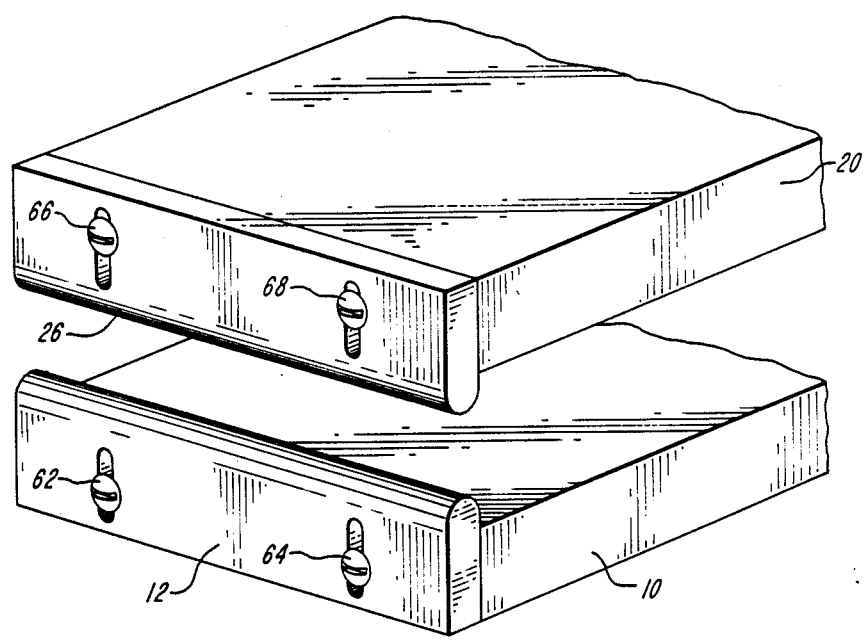
FIG. 4 shows a perspective view of the first and second compression plates of an alternative form of the breast compression assembly of the invention.

In one embodiment, as shown in FIG. 4, the height of the ridge member above the surface of the plate can be varied according to the dimensions of the specific breast to be imaged. In this embodiment the ridge members 14 and 24 are held in place by screws 62, 64, 66, and 68, respectively, which pass through vertically extending slots in respective members 12 and 26. The relative heights of members 12 and 26 may be controlled by suitably adjusting the position, and then anchoring the members 12 and 26 in place with the screws. Alternatively, the ridge members may be permanently affixed to the plate(s) by, e.g., glue, or by the molding of the plate to include the ridge member.

Compression plates 10 and 20 may have substantially planar first and second compression surfaces or may have surfaces which have concave or convex regions for differential compression of the breast tissues. The plates and the ridge member may be constructed of a rigid material or of a firm but compressible or expandable material such as rubber or plastic. Compression plates used in an x-ray device are made of material which is substantially transparent to x-rays.

Imaging of the breast can be performed using the breast compression assembly system in a vertical, horizontal, or other configuration as desired.

The invention may be embodied in other specific forms without departing from the spirit or essential characteristics thereof. The present embodiments are therefore considered to be in all respects as illustrative and not restrictive, the sCope of the invention being indicated by the appended claims rather than by the foregoing description, and all changes which come within the meaning and range of equivalency of the claims are therefore intended to be embraced therein.

I claim:

1. A breast compression assembly for a mammography apparatus, comprising:
   (a) a first compression plate having a first compression surface extending from an input edge thereof;
   (b) a second compression plate having a second compression surface extending from an input edge thereof;
   wherein at least one of said first or second compression plates includes an associated ridge member extending from said input edge and beyond said compression surface of said associated plate at least partially in a direction substantially perpendicular to said surface at its input edge, and further comprising:
   (c) means for positioning said compression plates whereby said first compression surface of said first compression plate is opposite to said second compression surface of said second compression plate, and whereby said input edges of said first and second compression plates are substantially opposite each other; and
   (d) means for selectively controlling the separation between said compression surfaces along a reference axis substantially perpendicular to said surfaces;
   whereby a breast inserted between said input edges of said plates may be pulled away from the chest wall and captively held and compressed between said opposite compression surfaces by biasing said first and second compression plates toward each other and against said inserted breast.

2. A breast compression assembly according to claim 1 wherein each of said first compression plate and said second compression plate comprises one of said ridge members.

3. A breast compression assembly according to claim 1 further comprises means for adjustably positioning said ridge member of at least one of said compression plates at least partially in the direction perpendicular to said compression surface of said compression plate at said input edges.

4. A breast compression assembly according to claim 3 wherein said adjustable ridge member positioning means comprises means for adjustably positioning said ridge members of both of said first and second compression plates at least partially in the direction perpendicular to said compression surfaces of said plates at said input edges.

5. A breast compression assembly according to claim 1 wherein one of said first compression plate and said second compression plate comprises one of said ridge members.

6. A breast compression assembly according to claim 5 further comprising means for adjustably positioning said ridge member at least partially in a direction perpendicular to said compression surface of said compression plate at said input edge.

7. A breast compression assembly according to claim 1 wherein said first compression plate further comprises an integral x-ray detector.

8. A breast compression assembly according to claim 1 wherein one of said compression plates is rigid.

9. A breast compression assembly according to claim 1 wherein said first compression surface of said first compression plate is substantially planar.

10. A breast compression assembly according to claim 1 wherein said second compression surface of said second compression plate is substantially planar.

11. A breast compression assembly according to claim 1 wherein said first and second compression surfaces are substantially planar and said first compression surface is substantially parallel to said second compression surface.

12. A breast compression plate for a mammography apparatus, comprising:
a compression member having a compression surface extending from an input edge thereto; and
a ridge member extending from said input edge and beyond said compression surface at least partially in the direction substantially perpendicular to said compression surface at said input edge.

13. A breast compression plate according to claim 12 further comprising means for adjustably positioning said ridge member at least partially in a direction perpendicular to said compression surface of said compression plate at said input edge.

14. A breast compression plate according to claim 12 wherein said compression plate further comprises an integral x-ray detector.

15. A breast compression plate according to claim 12 wherein said compression plates is rigid.

16. A breast compression plate according to claim 12 wherein said compression surface of said compression plate is substantially planar.

17. A breast compression plate according to claim 12 wherein said compression member and said ridge member are integral.

18. A breast compression plate according to claim 12 wherein said compression member is substantially optically transparent

* * * * *